United States Patent [19]

Takahashi et al.

[11] Patent Number: 5,859,260
[45] Date of Patent: Jan. 12, 1999

[54] PROCESS FOR PREPARING IMIDAZOLE DERIVATIVE

[75] Inventors: Toshiya Takahashi; Yasunobu Miyamoto; Masahiko Mizuno; Norihiko Hirata, all of Osaka, Japan

[73] Assignee: Sumitomo Chemical Company, Limited, Osaka, Japan

[21] Appl. No.: 768,630

[22] Filed: Dec. 18, 1996

[30] Foreign Application Priority Data

Dec. 20, 1995 [JP] Japan ................................. 7-331745
Oct. 18, 1996 [JP] Japan ................................. 8-276401

[51] Int. Cl.$^6$ ........................ C07D 495/04; C07D 493/04
[52] U.S. Cl. ............................ 548/303.7; 548/303.1
[58] Field of Search ........................... 548/303.1, 303.7

[56] References Cited

U.S. PATENT DOCUMENTS 5,498,721 3/1996 Mizuno et al. ..................... 548/303.7

OTHER PUBLICATIONS

Acc. No. #95–330776, Japio, "Production of Biotin, etc" Dec. 1995.

Primary Examiner—Patricia L. Morris
Attorney, Agent, or Firm—Sughrue, Mion, Zinn, Macpeak & Seas, PLLC

[57] ABSTRACT

An imidazole derivative of the general formula (1):

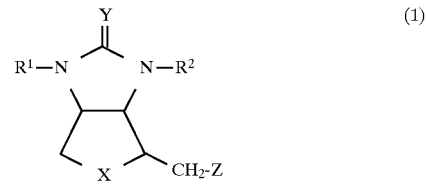

wherein $R^1$ and $R^2$ are each a hydrogen atom or an alkyl, aryl, acyl or aralkyl group, X and Y are each an oxygen or sulfur atom, and Z is a substituted alkyl group is prepared by reducing a thienoimidazole carboxylic acid of the general formula (2):

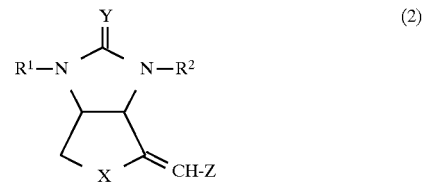

in an alcoholic solvent using a palladium catalyst, adding an adsorbent and an ion exchange resin, chelate resin or polymeric flocculating agent to the reaction mixture, and removing the spent catalyst from the reaction mixture.

12 Claims, No Drawings

PROCESS FOR PREPARING IMIDAZOLE DERIVATIVE

BACKGROUND OF THE INVENTION

1. Field of the Invention

The present invention relates to an industrially advantageous process for preparing an imidazole derivative which is useful as an intermediate for the preparation of biotin (vitamin H).

2. Description of Prior Art

JP-A-61-151194 discloses a process for the preparation of an imidazole derivative of the formula (1):

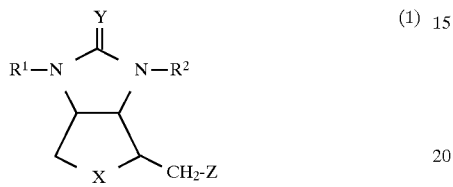

wherein $R^1$ and $R^2$ are the same or different and each represents a hydrogen atom or an alkyl, aryl, acyl or aralkyl group, X and Y are the same or different and each an oxygen or sulfur atom, and Z is a substituted alkyl group, which comprises catalytically reducing a corresponding precursor in an alcoholic solvent using a palladium catalyst. The palladium catalyst has the superior catalytic activity to other catalysts, while removal of the spent catalyst from the reaction mixture is difficult. Therefore, the above disclosed process removes the spent catalyst from the reaction mixture by replacing the alcoholic solvent with other solvent such as toluene.

However, the above disclosed process is not satisfactory as the industrial process since it requires the troublesome and time consuming procedures for the evaporation of the alcoholic solvent and the addition of the other solvent, and also the number of process steps such as the steps for recovering and recycling the solvents increases because of the use of a plurality of the solvents.

SUMMARY OF THE INVENTION

An object of the present invention is to provide an industrially advantageous process for preparing an imidazole derivative of the above formula (1) through the catalytic reduction of a corresponding precursor in an alcoholic solvent using a palladium catalyst, in which the spent catalyst can be removed from the reaction system without changing the kind of the solvent after the reaction.

Accordingly, the present invention provides a process of preparing an imidazole derivative of the general formula (1):

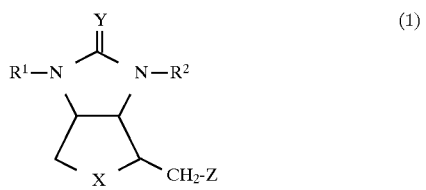

wherein $R^1$ and $R^2$ are the same or different and each represents a hydrogen atom or an alkyl, aryl, acyl or aralkyl group, X and Y are the same or different and each represents an oxygen or sulfur atom, and Z is a substituted alkyl group, comprising the steps of:

catalytically reducing a thienoimidazole carboxylic acid of the general formula (2):

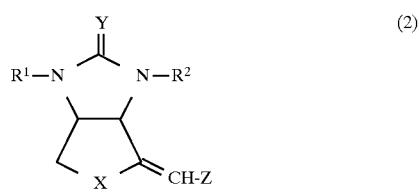

wherein $R^1$, $R^2$, X, Y and Z are the same as defined above in a solvent selected from the group consisting of alcohols and mixtures of alcohols and water using a palladium catalyst, adding an adsorbent and at least one material selected from the group consisting of ion exchange resins, chelate resins and polymeric flocculating agents to the reaction mixture obtained in the above step, and removing the spent catalyst from the reaction mixture.

DETAILED DESCRIPTION OF THE INVENTION

The thienoimidazole carboxylic acid of the general formula (2) may be an optically active compound or a racemic body.

For the $R^1$ and $R^2$ groups in the above formulas (1) and (2), the alkyl group may be an alkyl group having 1 to 8 carbon atoms, and the aryl groups may be a phenyl or naphthyl group which may have at least one substituent such as an alkyl group having 1 to 6 carbon atoms, an alkoxy group having 1 to 6 carbon atoms or a halogen atom (e.g. a fluorine, chlorine or iodine atom).

The acyl group may be an alkylcarbonyl group having 2 to 9 carbon atoms such as an acetyl, propionyl, butyryl or valelyl group, and the aralkyl group may be a phenylalkyl group having 1 to 12 carbon atoms in the alkyl group.

The alkyl group in the Z group may be an alkyl group having 1 to 8 carbon atoms, and the substituent may be a halogen atom (e.g. a fluorine atom, chlorine atom or bromine atom, a hydroxyl group, a carboxyl group, an alkoxy group having 1 to 8 carbon atoms or an alkoxycarbonyl group having 2 to 9 carbon atoms.

In the process of the present invention, conventional ion exchange resins, chelate resins and polymeric flocculating agents can be used.

The ion exchange resins include strong acid, weak acid, strong base and weak base types according to the chemical natures, or styrenic, acrylic and phenolic resin types according to the components, or gel and macroporous types according to the structures.

The chelate resins include weak base and chelating types according to the chemical natures, or acrylic, pyridinic and styrenic types according to the components.

The polymeric flocculating agents include polyacrylamide, polyacryl ester, polyacrylamide, melamine and carbamate types according to the components, or nonionic, anionic and cationic types according to the ionic natures. The molecular weight may be in the range between 1,200,000 and 17,000,000.

Among the above materials, the strongly acidic ion exchange resins, in particular the macroporous strongly acidic ion exchange resins having a wide service temperature range and a wide effective pH range are preferable because of the good flocculating properties.

Examples of the adsorbent are activated carbon, activated clay, diatomaceous earth, silica gel, alumina and the like. Among them, activated carbon is preferable.

The adsorbent has good properties for decoloration and removal of impurities in addition to the properties for flocculating and adsorbing the spent catalyst.

The reaction solvent is an alcohol or a mixture of the alcohol and water. Examples of the alcohol are methanol, ethanol, 2-propanol, and the like. Among them, 2-propanol is preferable. The weight ratio of water to the alcohol is usually between 0.01:1 and 5:1, preferably between 0.05:1 and 3:1, more preferably between 0.05:1 and 1:1.

The reaction mixture may contain other solvents such as hydrocarbons (e.g. toluene) in an acceptable amount.

The palladium catalyst may be any conventional one which is used for catalyzing the above reaction.

Examples of the palladium catalyst are inorganic salts of palladium such as palladium oxide, palladium chloride, palladium sulfate, palladium nitrate, and the like; and organic palladium compounds such as palladium acetate, palladium propionate, dichlorobis(triphenylphosphine) palladium, di-$\mu$-chlorobis($\eta$-allyl)-palladium, dichloro($\eta$-1,5-cyclooctadiene)palladium, dichloro($\eta$-2,5-norbornadiene) palladium, dichlorobis(acetonitrile)palladium, dichlorobis (benzonitrile)palladium, dichlorobis(N,N-dimethyl-formamide)palladium, bis(acetylacetonato)palladium, bis (dimethyl-glyoxymato)palladium, and the like. They may be used independently or in admixture. Among them, the organic palladium compound, in particular, palladium acetate is preferable.

In general, the catalytic reduction of the thienoimidazole carboxylic acid (2) is carried out by adding the thienoimidazole carboxylic acid (2) and the palladium catalyst in the solvent to give a mixture and then supplying hydrogen to the mixture. The reaction is usually performed in an autoclave in the hydrogen atmosphere under pressure.

The amount of the palladium catalyst is at least 0.05 wt. %, preferably at least 0.4 wt. % based on the weight of the thienoimidazole carboxylic acid (2). The upper limit of the amount of the catalyst is not critical, and is preferably at most 1 wt. % from the economical point of view.

The amount of the solvent is not limited.

The reaction temperature is usually between 0° and 100° C., preferably between 30° and 70° C.

The hydrogen pressure is usually between 1 and 100 kg/cm$^2$, preferably between 5 and 30 kg/cm$^2$.

The reaction time is usually between 30 minutes and 4 hours.

The termination of the reduction can be confirmed by the consumption of the raw material by liquid chromatography, while it can be conveniently confirmed by the termination of hydrogen consumption.

After the completion of the reduction, the reaction mixture is treated with the adsorbent and at least one material selected from the group consisting of the ion exchange resins, chelate resins and polymeric flocculating agents, and then filtrated to remove the spent catalyst from the reaction mixture.

The above treatment may be performed by adding the adsorbent and the above material to the reaction mixture and optionally maintaining the reaction mixture at a certain temperature of, for example, between 0° and 100° C., preferably between 30° and 70° C. for 30 minutes to 4 hours.

The amount of the at least one material selected from the group consisting of the ion exchange resins, chelate resins and polymeric flocculating agents is usually at least 0.01 wt. part, preferably at least 0.1 wt. parts per one wt. part of the palladium catalyst. The upper limit of the amount of the above material is not limited, and is usually at most 10 wt. parts per one wt. part of the palladium catalyst.

The amount of the adsorbent is usually at least 0.1 wt. part, preferably at least 1 wt. part per one wt. part of the palladium catalyst. The upper limit of the amount of the adsorbent is not limited, and is usually at most 30 wt. parts per one wt. part of the palladium catalyst.

The flocculation of the spent catalyst in the above treatment can be accelerated by the heating of the reaction mixture at a temperature higher than the temperature for the reduction reaction, for example, between 80° and 300° C. for 30 minutes to 4 hours, prior to the above treatment for flocculation.

The reaction mixture which has been subjected to the above flocculation treatment is filtrated by a conventional method such as filtration under reduced or increased pressure, and the spent catalyst can be easily removed from the mixture in a short time.

After the filtration, the solvent is evaporated off from the reaction mixture to recover the imidazole derivative (1). The imidazole derivative (1) can be purified by, for example, column chromatography or recrystallization, if necessary.

The imidazole derivative (1) can be converted to biotin or a derivative thereof by the known method, for example, by heating it in methanesulfonic acid as described in JP-B-63-8954 (=U.S. Pat. No. 4,537,973).

The process of the present invention can solve the problems encountered in the filtration step in the conventional processes for the preparation of the imidazole derivative (1) and effectively produces the imidazole derivative (1) at the high yield without performing the troublesome procedures such as the replacement of the solvents and recovery of the several solvents.

EXAMPLES

The present invention will be illustrated by the following examples, which do not limit the scope of the present invention in any way.

Example 1

5-((3aS,6aR)-4,6-Dibenzyl-5-oxohexahydro-1H-thieno [3,4-d]imidazol-1-ylidene)pentanoic acid (40 g) was dissolved in the mixture of 2-propanol (56 g) and water (6.3 g) and catalytically reduced with hydrogen in the presence of palladium acetate (0.32 g, 0.8 wt. %) under hydrogen pressure of 20 kg/cm$^2$ in an autoclave heated at 55° C. for 3 hours.

After the reduction, the reaction mixture was heated to 80° C. and kept at that temperature for 2 hours. Then, the ion exchange resin (Duolite™ CC-265H, 0.32 g) and activated carbon (2 g) were added to the reaction mixture and stirred at 60° C. for 2 hours, followed by filtration off of the spent catalyst. The filtrate was decolorized from 16 to 5 in the Gardner Color Scale by the addition of the activated carbon.

The filtrate was concentrated under reduced pressure to obtain 5-((1R,3aS,6aR)-4,6-dibenzyl-5-oxohexahydro-1H-thieno[3,4-d]imidazol-1-yl)pentanoic acid (39.2 g) as the oil.

The produced compound was crystallized by keeping it in a refrigerator overnight.

Further, the compound was recrystallized from 2-propanol and hexane, and the recrystallized compound had the melting point of 91°–92° C. and $[\alpha]_d^{20}$ of −26.8° (c=1.0, methanol).

Example 2

(3aS,6aR)-4,6-Dibenzyl-1-(3-ethoxypropylidene)-5-oxohexahydro-1H-thieno[3,4-d]imidazole (40 g) was dissolved in the mixture of 2-propanol (56 g) and water (6.3 g) and catalytically reduced with hydrogen in the presence of palladium acetate (0.32 g, 0.8 wt. %) under hydrogen pressure of 20 kg/cm$^2$ in an autoclave heated at 55° C. for 3 hours.

After the reduction, the reaction mixture was heated to 80° C. and kept at that temperature for 2 hours. Then, the ion exchange resin (Duolite™ CC-265H, 0.32 g) and activated carbon (2 g) were added to the reaction mixture and stirred at 60° C. for 2 hours, followed by filtration off of the spent catalyst. The filtrate was decolorized from 16 to 5 in the Gardner Color Scale by the addition of the activated carbon.

The filtrate was concentrated under reduced pressure to obtain (1R,3aS,6aR)-4,6-dibenzyl-1-(3-ethoxypropyl)-5-oxohexahydro-1H-thieno[3,4-d]imidazole (39.2 g) as the oil.

Example 3

(3aS,6aR)-4,6-Dibenzyl-1-(3-ethoxypropylidene)-5-oxohexahydro-1H-thieno[3,4-d]imidazole (40 g) was dissolved in the mixture of 2-propanol (56 g), toluene (5 g) and water (6.3 g) and catalytically reduced with hydrogen in the presence of palladium acetate (0.32 g, 0.8 wt. %) under hydrogen pressure of 20 kg/cm$^2$ in an autoclave heated at 55° C. for 3 hours.

After the reduction, the reaction mixture was heated to 80° C. and kept at that temperature for 2 hours. Then, the ion exchange resin (Duolite™ CC-265H, 0.32 g) and activated carbon (2 g) were added to the reaction mixture and stirred at 60° C. for 2 hours, followed by filtration off of the spent catalyst. The filtrate was decolorized from 16 to 5 in the Gardner Color Scale by the addition of the activated carbon.

The filtrate was concentrated under reduced pressure to obtain (1R,3aS,6aR)-4,6-dibenzyl-1-(3-ethoxypropyl)-5-oxohexahydro-1H-thieno[3,4-d]imidazole (39.2 g) as the oil.

Example 4

The reaction and post-treatment were performed in the same manners as in Example 1 except that activated clay (2 g) was used in place of activated carbon (2 g), and 5-((1R,3aS,6aR)-4,6-dibenzyl-5-oxohexahydro-1H-thieno[3,4-d]imidazol-1-yl)pentanoic acid (39.2 g) was obtained as the oil.

Example 5

The reaction and post-treatment were performed in the same manners as in Example 1 except that the chelate resin (SUMICHELATE MC-75, 0.32) was used in place of the ion exchange resin, and 5-((1R,3aS,6aR)-4,6-dibenzyl-5-oxohexahydro-1H-thieno[3,4-d]imidazol-1-yl)pentanoic acid (39.2 g) was obtained as the oil.

Comparative Example 1

The reaction and post-treatment were performed in the same manner as in Example 1 except that aluminum sulfate (10 g) and activated carbon (7.5 g) were used in place of the ion exchange resin (0.32 g) and activated carbon (2 g), and the desired compound (39 g) was obtained.

Example 6

The filtration times for filtrating the reaction mixtures which had been treated with the combination of the adsorbent and the ion exchange resin, chelate resin or polymeric flocculating in Examples 1 and 5 and Comparative Example 1 were ed. The results are shown in the Table.

TABLE

| Example No. | Additive | Adsorbent | Filt-ration time (min.) |
| --- | --- | --- | --- |
| 1 | Ion exchange resin (0.32 g) | Activated carbon (2.0 g) | 15 |
| 5 | Chelate resin (0.32 g) | Activated carbon (2.0 g) | 15 |
| C. 1 | Aluminum sulfate (10 g) | Activated carbon (7.5 g) | 89 |

What is claimed is:

1. A process of preparing an imidazole derivative of the formula (1):

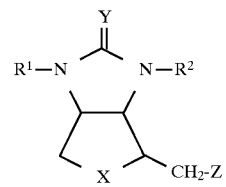

wherein R$^1$ and R$^2$ are the same or different and each represents a hydrogen atom, an alkyl group, a phenyl or napthyl group which may optionally have at least one substituent selected from the group consisting of an alkyl group having 1 to 6 carbon atoms, an alkoxy group having 1–6 carbon atoms and a halogen atom, an alkylcarbonyl group having 2 to 9 carbon atoms; or a phenylalkyl group having 1 to 12 carbon atoms in the alkyl group, X and Y are the same or different and each represents an oxygen or sulfur atom, and Z is an alkyl group having 1 to 8 carbon atoms which may optionally have at least one substituent selected from the group consisting of a halogen atom, a hydroxyl group, a carboxyl group, an alkoxy group having 1 to 8 carbon atoms and an alkoxycarbonyl group having 2 to 9 carbon atoms, comprising the steps of:

catalytically reducing an imidazole derivative of the formula (2):

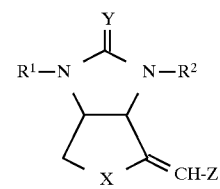

wherein R$^1$, R$^2$, X, Y and Z are the same as defined above in a solvent selected from the group consisting of an alcohol and mixtures of an alcohol and water using a palladium catalyst, adding an adsorbent and at least one material selected from the group consisting of ion exchange resins, chelate resins and polymeric flocculating agents to the reaction mixture obtained in the above step, and removing the spent catalyst from the reaction mixture.

2. The process according to claim 1, wherein said palladium catalyst is an organic palladium compound.

3. The process according to claim 2, wherein said organic palladium compound is at least one compound selected from the group consisting of palladium acetate, palladium propionate, dichlorobis(triphenylphosphine)palladium, di-μ-chlorobis(η-allyl)-palladium, dichloro(η-1,5-cyclooctadiene)palladium, dichloro(η-2,5-norbornadiene)palladium, dichlorobis(acetonitrile)palladium, dichlorobis(benzonitrile)palladium, dichlorobid(N,N-dimethylformamide)palladium, bis(acetylacetonato)palladium and bis(dimethylglyoxymato)palladium.

4. The process according to claim 1, wherein said palladium catalyst is an inorganic salt of palladium.

5. The process according to claim 4, wherein said inorganic salt of palladium is at least one salt selected from the group consisting of palladium oxide, palladium chloride, palladium sulfate and palladium nitrate.

6. The process according to claim 1, wherein said at least one material is an ion exchange resin.

7. The process according to claim 6, wherein said ion exchange resin is a strong acid ion exchange resin.

8. The process according to claim 1, wherein said adsorbent is activated carbon.

9. The process according to claim 1, which further comprises heating the reaction mixture at a temperature higher than the temperature for the reduction reaction.

10. The process according to claim 1, wherein $R^1$ and $R^2$ in the formulas (1) and (2) are both benzyl groups.

11. The process according to claim 1, wherein X is a sulfur atom and Y is an oxygen atom in the formulas (1) and (2).

12. The process according to claim 1, wherein Z is a 3-carboxypropyl or 2-ethoxyethyl group.

* * * * *